US00PP25033P3

(12) United States Plant Patent
Suphachadiwong

(10) Patent No.: US PP25,033 P3
(45) Date of Patent: Nov. 4, 2014

(54) ***PHALAENOPSIS* PLANT NAMED 'SUPHAL1311'**

(50) Latin Name: ***Phalaenopsis* hybrid**
Varietal Denomination: SUPHAL1311

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 40 days.

(21) Appl. No.: 13/815,794

(22) Filed: Mar. 15, 2013

(65) Prior Publication Data

US 2014/0283258 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1311' is disclosed, characterized by dark green with very small brown dots stem color, sepals and petals colored white with purple netting and lip and side lobes which are white with strong purple netting and yellow coloration. The new variety is a *Phalaenopsis*, typically produced as an indoor ornamental plant.

2 Drawing Sheets

Figure 1:
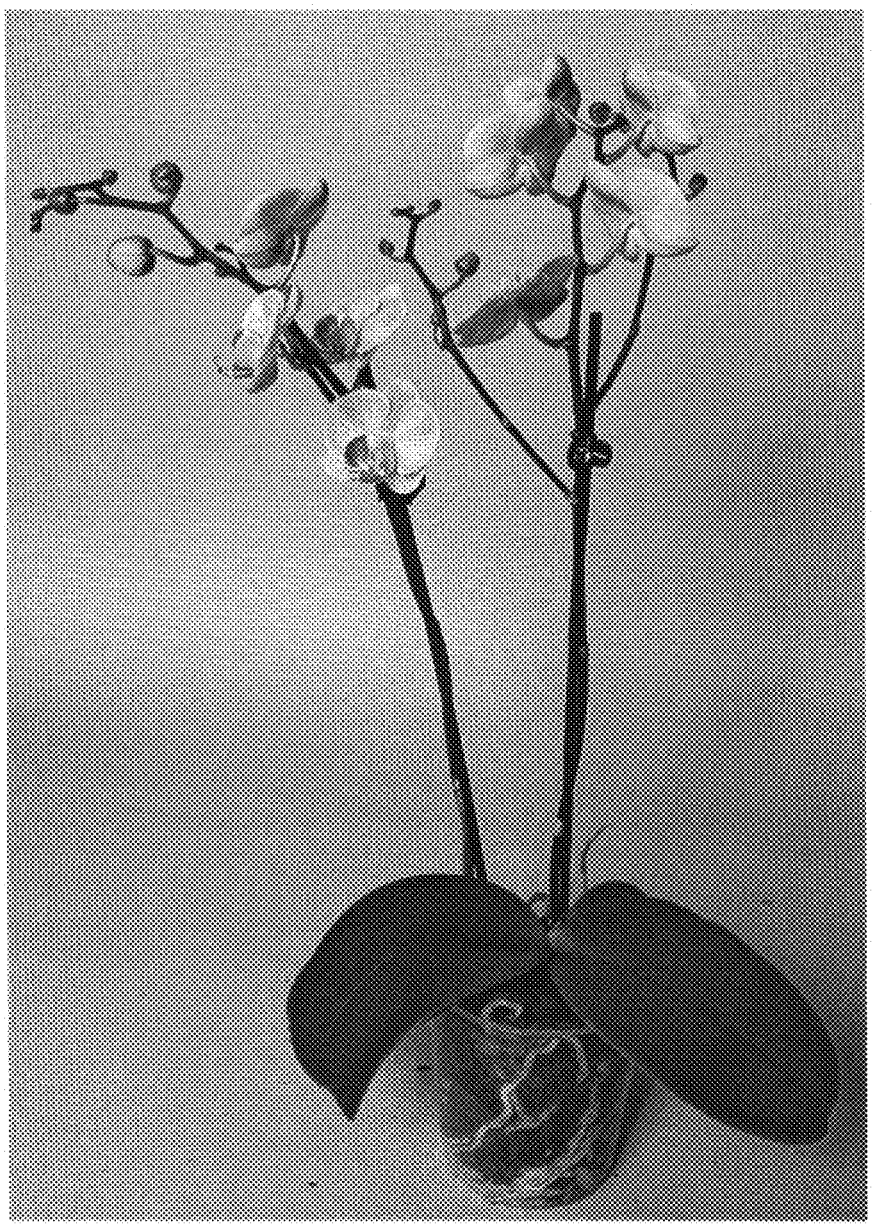

Latin name of the genus and species: *Phalaenopsis* hybrid. Variety denomination: 'SUPHAL1311'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'PD24S2' with the unpatented, proprietary pollen parent referred to as *Phalaenopsis* 'PFM1'. The crossing was made by the inventor in his research greenhouse in Chonburi, Thailand in January of 2005.

The new variety was first selected by the inventor, Thumrong Suphachadiwong, a citizen of Thailand, in December of 2007 in a research greenhouse belonging to the inventor in Chonburi, Thailand. After identifying the new variety as a potentially interesting selection, the inventor continued confidential testing and propagation of 'SUPHAL1311', assessing stability of the unique characteristics of this variety.

Asexual reproduction of the new cultivar 'SUPHAL1311' was first performed at a commercial laboratory belonging to the inventor in Chonburi, Thailand by tissue culture in July of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1311' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1311'. These characteristics in combination distinguish 'SUPHAL1311' as a new and distinct *Phalaenopsis* cultivar:

1. Sepal and petal color is white with purple netting.
2. Lip and side lobes are white with strong purple netting and yellow coloration.
3. Dark green peduncle with brown spots.

PARENT COMPARISON

Plants of the new cultivar 'SUPHAL1311' are similar to the seed parent, *Phalaenopsis* 'PD24S2' in most horticultural characteristics. The new variety, however, produces smaller flowers with striped color compared to the larger, solid white flowers of the seed parent. Additionally the new variety produces a smaller plant size compared to the seed parent.

Plants of the new cultivar 'SUPHAL1311' are similar to the pollen parent, *Phalaenopsis* 'PFM1' in most horticultural characteristics. Plants of the new variety however produce a larger and lighter colored flower as well as a larger plant size than the pollen parent.

COMMERCIAL COMPARISON

'SUPHAL1311' is similar to the unpatented commercial variety *Phalaenopsis* 'F2428' in most horticultural characteristics. However the new variety, 'SUPHAL1311' differs from 'F2428' in the following characteristics:

1. Netting is weaker.
2. Larger flower size.
3. Different lateral sepal shape.
4. Different apical lobe shape.

5. Different dorsal sepal shape.
6. Taller plant height.

BRIEF DESCRIPTION OF THE PHOTOGRAPH

The accompanying photographs in FIG. 1 illustrates in full color a typical plant of 'SUPHAL1311' grown in a commercial greenhouse in Zuidbroek, the Netherlands. This plant is approximately 18 months old after deflasking, shown planted in an 11 cm container.

Figure 2:
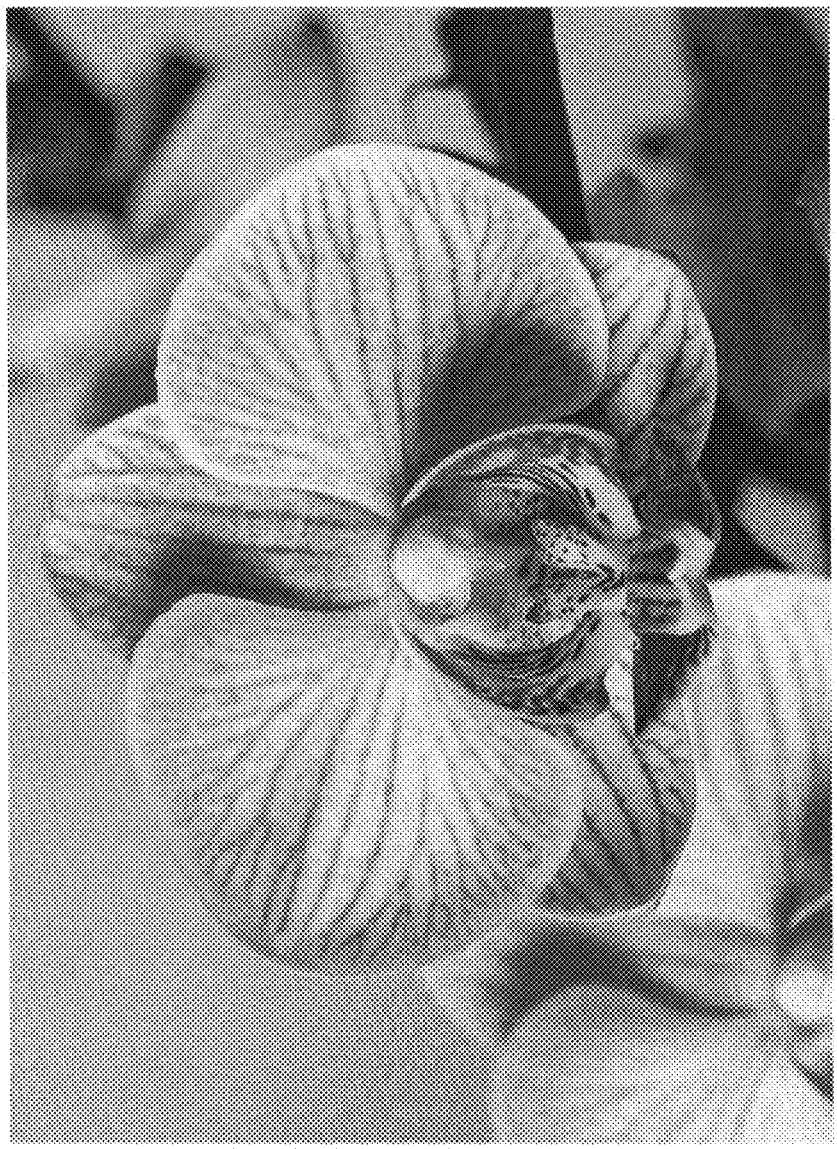

FIG. 2 illustrates a close up of the individual flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1311' plants grown in a commercial greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1311'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 194A to 194B.

PLANT

Growth habit: Monopodial.

Height from top of soil line to top of foliage: Average 5.4 cm.

Height from top of soil line to top of flowers: Average 41.6 cm.

Plant spread: At widest, average: 32.8 cm; at narrowest: 24.0 cm.

Normal pot size: 11 cm.

Growth rate: Moderate.

Number of leaves per plant: Average 6.

FOLIAGE

Leaf:

*Arrangement*.—Distichous.

*Average length*.—Approximately 14.7 cm (including sheath).

*Average width*.—Approximately 7.4 cm.

*Shape of blade*.—Elliptic.

*Aspect*.—Horizontal to slightly curled downward.

*Apex*.—Unequal acute, slightly pointed downward.

*Base*.—Cuneate. Sheath length: Average 1.2 cm. Sheath width: Average 0.8 cm. Sheath color: Yellow-green; near RHS 144A to 144B.

*Margin*.—Entire.

*Texture of top surface*.—Smooth, very slightly furrowed.

*Texture of bottom surface*.—Smooth.

*Appearance*.—Glossy on both surfaces.

*Color*.—Young foliage upper side: Green; near RHS N137B. Young foliage under side: Yellow-green; in between near RHS 146B and 147B. Mature foliage upper side: Green; near RHS N137B. Mature foliage under side: Yellow-green; in between near RHS 146B and 147B.

*Venation*.—Type: Camptodromous. Venation coloration: Upper side green; near RHS N137B, under side yellow-green; in between near RHS 146B and 147B, main vein on under side green; near RHS 137A.

Petiole: No petiole present.

FLOWERING CHARACTERISTICS

Flower bud:

*Rate of opening*.—Approximately one week after stage described.

*Length*.—Approximately 1.5 cm.

*Diameter*.—Approximately 1.2 cm wide and 1.4 cm high.

*Shape*.—Broad ovate.

*Color*.—Green; near RHS 146D, tinged greyed-orange on upper side; near RHS 177B.

Peduncle:

*Length*.—Approximately 51.2 cm.

*Width*.—Approximately 0.5 cm.

*Aspect*.—Approximately 60° angle to rosette.

*Strength*.—Strong.

*Texture*.—Smooth.

*Appearance*.—Matte.

*Color*.—Yellow-green; near RHS 146B, densely covered with very small brown dots; near RHS 200A.

Inflorescence:

*Flowers per stem*.—Average 23.

*Inflorescence arrangement*.—Compound panicle.

*Inflorescence height*.—Approximately 18.5 cm (measured from lowest branching of panicle to top of inflorescence).

*Inflorescence width*.—Approximately 16.5 cm.

Individual flowers:

*Flower type*.—Single zygomorphic flower.

*Shape*.—Rounded deltate.

*Length* (*height*).—Approximately 4.9 cm.

*Width*.—Approximately 5.3 cm.

*Depth*.—Approximately 2.3 cm.

*Fragrance*.—No fragrance.

*Persistent*.—Non-persistent.

*Quantity of petals*.—2 true petals.

Petals:

*Arrangement*.—One petal on each side of the column.

*Length*.—Approximately 2.5 cm.

*Width*.—Approximately 3.1 cm.

*Shape*.—Deltoid.

*Apex*.—Obtuse.

*Base*.—Cuneate.

*Margin*.—Entire.

*Texture*.—Upper (forward) surface: Smooth, velvety.

*Texture*.—Lower (back) surface: Smooth, velvety.
*Appearance*.—Matte on both surfaces.
*Color*.—When opening, forward surface: Purple to white; in between RHS 76D and N155A, margins white; near RHS 155C. When opening, back surface: White; near RHS 155C. Fully Opened, forward surface: Purple to white; in between RHS 76D and N155A, margins white; near RHS 155C. Fully Opened, back surface: White; near RHS NN 155C. Fading, forward surface: Not fading, only becoming non-velvety. Fading, back surface: Not fading, only becoming non-velvety.
*Color venation*.—Fully Opened, forward surface: Purple; near RHS N78B and N78C. Fully Opened, back surface: Purple; near RHS N78D.

Labellum:
*Shape*.—Three-parted.
*Length*.—Approximately 2.1 cm.
*Width*.—Approximately 1.8 cm.
*Texture*.—Smooth, slightly velvety.
*Appearance*.—Matte.
*Tip*.—Cleft, tips cirrhose, curled upward.
*Base*.—Cuneate.
*Color*.—When opening, forward surface: Central lobe white; near RHS N155D, base yellow; near RHS 13B and 13C; tinged and veined purple and yellow-orange; near RHS N78B and 22B, lateral lobes white; near RHS N155C, heavily veined and tinged purple; near RHS N78B, lower margin yellow; near RHS 13C, callosities yellow; near RHS 11C, dotted greyed-purple; near RHS N186C. When opening, back surface: Central lobe white; near RHS N155B, tinged yellow-green towards the base; near RHS 150D and greyed-purple at the margins; near RHS 184B, lateral lobes purple; near RHS 76B, base white; near RHS 155C lower margin yellow; near RHS 11B. Fully Opened, forward surface: Central lobe white; near RHS N155D, base yellow; near RHS 13B and 13C; tinged and veined purple and yellow-orange; near RHS N78A and N78B and 22A and 22B, lateral lobes white; near RHS N155C, heavily veined and tinged purple; near RHS N78A, lower margin yellow; near RHS 13B, callosities yellow; near RHS 11B and 11C, dotted greyed-purple; near RHS N186C. Fully Opened, back surface: Central lobe white; near RHS N155B, tinged yellow-green towards the base; near RHS 150D and greyed-purple at the margins; near RHS 184B, lateral lobes purple; near RHS 76C, base white; near RHS 155C lower margin yellow; near RHS 11C. Fading, forward surface: Not fading, only becoming non-velvety. Fading, back surface: Not fading, only becoming non-velvety.
*Color venation*.—Fully Opened, forward surface: Purple and yellow-orange; near RHS N78A and N78B and 22A and 22B. Fully Opened, back surface: No venation visible. Margin: Entire.

Sepals:
*Quantity*.—3.
*Length*.—Approximately 2.7 cm.
*Width*.—Approximately 2.0 cm.
*Shape*.—Ovate.
*Apex*.—Broad bluntly acute.
*Base*.—Broad cuneate.
*Margin*.—Entire.
*Texture*.—Smooth, velvety.
*Appearance*.—Matte.
*Color*.—Fully Opened, forward surface: Purple to white; in between RHS 76D and N155A, margins white; near RHS 155C, veined purple; near RHS N78B and N78C, lateral sepals finely dotted red-purple at the base; near RHS 71B. Fully Opened, back surface: Purple; in between RHS 75B and 76B, only slightly veined red-purple; 73A.

Pedicels:
*Length*.—Approximately 2.9 cm.
*Diameter*.—Approximately 0.3 cm.
*Angle*.—Approximately 85° to peduncle.
*Strength*.—Moderately strong.
*Texture*.—Smooth.
*Appearance*.—Moderately glossy.
*Color*.—Yellow-green; near RHS 152D, distal part greyed-purple; 186D.

REPRODUCTIVE ORGANS

Stamens, style and stigma fused into column?: Yes.
*Column length*.—Approximately 0.9 cm.
*Column diameter*.—Approximately 0.6 cm.
*Column color*.—Purple; near RHS 75A.

Ovary:
*Position*.—Inferior.
*Diameter*.—Approximately 0.3 cm.
*Color*.—White; near RHS NN155D.

Pollen color: Yellow-orange; near RHS 21A.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1311' as herein illustrated and described.

* * * * *